(12) United States Patent
Carreira et al.

(10) Patent No.: US 9,402,404 B2
(45) Date of Patent: Aug. 2, 2016

(54) USE OF A COMPOSITION COMPRISING AN ANTIMICROBIAL PEPTIDE AS A FOOD PRESERVATIVE

(71) Applicants: Alexandra Carreira, Cantanhede (PT); Sara Valadas Da Silva Monteiro, Cantanhede (PT); Ricardo De Seixas Boavida Ferreira, Cantanhede (PT)

(72) Inventors: Alexandra Carreira, Cantanhede (PT); Sara Valadas Da Silva Monteiro, Cantanhede (PT); Ricardo De Seixas Boavida Ferreira, Cantanhede (PT)

(73) Assignee: Consumo Em Verde—Biotecnologia Das Plantas, S.A., Cantanhede (PT)

( * ) Notice: Subject to any disclaimer, the term of this patent is extended or adjusted under 35 U.S.C. 154(b) by 0 days.

(21) Appl. No.: 14/752,984

(22) Filed: Jun. 28, 2015

(65) Prior Publication Data

US 2015/0289529 A1    Oct. 15, 2015

Related U.S. Application Data

(63) Continuation of application No. 13/879,162, filed as application No. PCT/EP2011/006782 on Oct. 12, 2011, now Pat. No. 9,095,166.

(30) Foreign Application Priority Data

Oct. 12, 2010  (PT) .......................................... 105331
Oct. 13, 2010  (GB) .................................. 1017283.1

(51) Int. Cl.

| | |
|---|---|
| *A23L 3/3526* | (2006.01) |
| *A23B 7/155* | (2006.01) |
| *A21D 2/26* | (2006.01) |
| *A21D 15/08* | (2006.01) |
| *A23B 4/20* | (2006.01) |
| *A23B 7/154* | (2006.01) |
| *A23B 9/26* | (2006.01) |
| *A23C 3/08* | (2006.01) |
| *A23L 3/3463* | (2006.01) |
| *A01N 47/44* | (2006.01) |
| *A01N 65/20* | (2009.01) |

(52) U.S. Cl.
CPC ................ *A23B 7/155* (2013.01); *A01N 47/44* (2013.01); *A01N 65/20* (2013.01); *A21D 2/267* (2013.01); *A21D 15/08* (2013.01); *A23B 4/20* (2013.01); *A23B 7/154* (2013.01); *A23B 9/26* (2013.01); *A23C 3/08* (2013.01); *A23L 3/3463* (2013.01); *A23L 3/34635* (2013.01); *A23L 3/3526* (2013.01); *A23V 2002/00* (2013.01)

(58) Field of Classification Search
None
See application file for complete search history.

(56) References Cited

U.S. PATENT DOCUMENTS

2003/0224939 A1* 12/2003 Miles ..................... A01N 25/00
                                                         504/206
2008/0300137 A1* 12/2008 De Seixas Boavida
                           Ferreira ............... C07K 14/415
                                                         504/189

* cited by examiner

*Primary Examiner* — Amber D Steele
*Assistant Examiner* — Schuyler Milton
(74) *Attorney, Agent, or Firm* — Adam Warwick Bell; Matthew Rupert Kaser

(57) ABSTRACT

The inventors provide the use of a composition comprising an antimicrobial polypeptide comprising Blad or an active variant thereof to prevent or inhibit spoilage of a foodstuff by a microorganism. Also provided is a method of preventing or inhibiting spoilage of a foodstuff by a microorganism comprising administering to a foodstuff in need thereof an effective amount of a composition comprising an antimicrobial polypeptide comprising Blad or an active variant thereof.

7 Claims, 2 Drawing Sheets

Figure 1

```
   1 gatggcgatg aatgaacact gcgtttgctg gctttgatga aaatcgagtg caacctaata
  61 taatcaaata tgggtaagat gagagtgagg tttccaacgt tagtgttggt actagaata
 121 gtattcctca tggcagtgtc aattggtatt gcttatggag aaaaagatgt gctaaagagt
 181 catgagaggc ctgaggaaag agaacaagag gagtggcaac ctaggagaca acgacctcaa
 241 agtagaaggg aagagagaga aagagagcaa gagcaggtt cagaggagtg agcagaggga
 301 cagagtggtt atgagaggag acaataccat gagaggagtg agcagaggga agagagagag
 361 caagaacaac aacaaggttc tccctcatac tcacgtagac aaaggaaccc ttatcacttc
 421 agctctcaaa gattccaaac tcttacaaa aataggaatg gcaaatccg tgtgtcgag
 481 aggtttgacc aaagaaccaa tagacttgag aatctccaaa actaccgcat tgttgagttc
 541 caatcaaaac ctaacactct cattctccct aaacactctg atgctgacta cgtcctcgtt
 601 gtactcaatg gtagagccac aatcacgata gtaaaccctg ataaagaaca agcatataac
 661 cttgagtatg gcgatgtctc cagaatccca gctggctcaa cttcatatat ccttaacccg
 721 gatgacaacc agaagcttag gtagtactaa ctcgcaatac tcctgctac tcctgctac
 781 ttttatgatt tctatccatc gagtactaaa gaccaacaat cctacttcag tggcttcagc
 841 aggaacactt tagaggccac cttcaatact cgttatgaag agatacaaag gattattta
 901 gggaatgagg atgagcaaga atatgaggaa caaaggcgtg ggcaacaaag gcaagaccaa
 961 gacgaggggg tgatagtgat agtttcaaag aaacagatcc aaaaattgac gagcgaccac
1021 caatctttcat caggaaaaga caacccctct gattctgcc ccttcaactt gagaagcaat
1081 gagcccatat attcaaacaa gtatgggaac ttctatgaaa tcactccaga tagaaaccct
1141 caagttcagg atttgaatat ctctctcacc tatataaaaa ttaacgaggg agctttgttg
1201 ttgccacact ataactcaaa ggccatatat gtagtcgtgg ttgatgaagg agaaggaaat
1261 tatgaactgg taggtattcg agatcaacaa cgacaacaag atgagcaaga agagaaagag
1321 gaagaagtga taggtatag tgctagatta tcagaaggtg acattttgt aattccagca
1381 ggttatccaa tttccatcaa tgcttcctca aatcttcgct tgcttggatt tggcatcaat
1441 gctgatgaaa accagaggaa tttcctcgca ggttctaaag acaatgtgat aaggcagtta
1501 gatagagcag tgaatgagct cacattccct ggttctgctg aagatattga gagattaatc
1561 aaaaccaac aacagtctta cttgcaaat ggtcagcctc aacaacaaca acaacaacaa
1621 agtgagaagg agggaagcg tggagaagcg ggttcatctc ttccattttg agcactttt
1681 actaagctgt tttaaaagct actatcatgt aagagctcat agtgagctac tgagagaata
1741 ataaaactaa agttggacct ttgtactaat aatgttaata aaaaaaaaaa a
```

Figure 2

```
  1 cgtagacaaa ggaaccctta tcacttcagc tctcaaagat tccaaactct ttacaaaaat
 61 aggaatggca aaatccgtgt gctcgagagg tttgaccaaa gaaccaatag acttgagaat
121 ctccaaaact accgcattgt tgagttccaa tcaaaaccta acactctcat tctccctaaa
181 cactctgatg ctgactacgt cctcgttgta ctcaatggta gagccacaat cacgatagta
241 aaccctgata gaagacaagc atataacctt gagtatggcg atgctctcag aatcccagct
301 ggctcaactt catatatcct taacccggat gacaaccaga agcttagagt agtcaagctc
361 gcaataccca tcaacaatcc tggctacttt tatgatttct atccatcgag tactaaagac
421 caacaatcct acttcagtgg cttcagcagg aacactttag aggccacctt caatactcgt
481 tatgaagaga tacaaaggat tattttaggg aatgaggat
```

USE OF A COMPOSITION COMPRISING AN ANTIMICROBIAL PEPTIDE AS A FOOD PRESERVATIVE

The present application is a continuation of pending application Ser. No. 13/879,162 filed 15 Jul. 2013 and claims priority to and the benefit of the following, to the extent allowable by law: U.S. application Ser. No. 13/879,162 filed 15 Jul. 2013, PCT/EP2011/067821, filed 12 Oct. 2011, and priority applications PT 105331 filed 12 Oct. 2010 and GB 1017283.1 filed 13 Oct. 2010, all of which, together with all references disclosed in this and all priority applications, are hereby incorporated by reference for all purposes.

A sequence listing text (.txt) file is submitted herewith under 37 CFR. 1.821(c) and hereby incorporated by reference in its entirely. The details of the file as required under 37 CFR. 1.52(e)(5) and 37 CFR 1.77(b)(5) are as follows: Name of file is P11336 WO_ST25.txt; date of creation is Friday, Jun. 26, 2015; size is 9.37 KB (9,605 bytes). The information recorded in electronic form (if any) submitted (under Rule 13ter if appropriate) with this application is identical to the sequence listing as contained in the application as filed.

FIELD OF THE INVENTION

The invention relates to the field of antimicrobial agents that target microorganisms that spoil food.

INTRODUCTION

Food preservation is the process of treating food to prevent or inhibit food spoilage caused by endogenous chemical/enzymatic degradation and/or caused or accelerated by a microorganism. A number of techniques exist for preserving food, some of which inhibit endogenous processes (e.g. antioxidants), some of which inhibit microbial processes (e.g. antimicrobials), and some of which inhibit both types of process (e.g. freezing). A compound that is used to inhibit food spoilage is commonly referred to as a preservative, which may be, for example an antioxidant or an antimicrobial.

Particular food preservation techniques include drying, heating, refrigerating or freezing, osmotic inhibition (e.g. use of syrups or salt), vacuum packing, canning and bottling, jellying, potting, jugging, ionising irradiation, pulsed electric field processing, high pressure food preservation, and ultra high water pressure food preservation, use of antioxidants, and/or use of antimicrobial preservatives (e.g. sulphur dioxide, carbon dioxide, ethanol, acetic acid, citric acid, lactic acid, sorbic acid, benzoates, nitrates and nitrites, sulphites, calcium propionate and methylchloroisothiazolinone).

Despite the relatively large number of food preservation techniques that are currently employed there is a need to develop new antimicrobial preservatives. This is because of the inadequacies of many pre-existing techniques to effectively target microorganisms and problems with efficacy and/or safety of many pre-existing antimicrobial preservatives in particular.

Many food preservation techniques that attempt to create non-favourable growth conditions for microorganisms are ineffective against organisms that survive in extreme conditions (e.g. *Pseudomonas* species can grow at very low temperatures; *Bacillus coagulans* is heat resistant and acid tolerant; many species of *Aspergillus* demonstrate oligotrophy; *Zygosaccharomyces* species have high xerotolerance).

Many pre-existing antimicrobial preservatives have moderate activity, especially against microorganisms with innate or acquired resistance, and/or narrow spectrum. For example, *Zygosaccharomyces* species have high tolerance to ethanol, acetic acid, sorbic acid, benzoic acid and sulphur dioxide. In addition, a number of pre-existing antimicrobial preservatives have been associated with various side-effects such as respiratory problems or ADD. In particular examples, sulphur dioxide is irritating to the bronchial tubes of asthmatics, nitrites are potentially carcinogenic, benzoates have been associated with various allergies, asthma, skin rashes and brain damage.

Furthermore, effective techniques for inhibiting microbial growth in food, such as low pH or low water activity, are often unacceptable to the consumer (e.g. give an acid taste) or have negative health implications (e.g. high salt or sugar).

It is among the objectives of the present invention to attempt a solution to these problems, and specifically for example to provide a new antimicrobial agent with potent and broad-spectrum activity against microorganisms whilst having low toxicity.

SUMMARY OF THE INVENTION

The inventors have surprisingly found that the Blad polypeptide from *Lupinus* shows potent antimicrobial activity against a large number of diverse bacterial and fungal organisms that cause food spoilage. The inventors have also found that the Blad polypeptide is non-toxic, therefore making Blad an excellent compound for use as an anti-microbial food preservative.

Accordingly, the inventors provide the use of a composition comprising an antimicrobial polypeptide comprising Blad or an active variant thereof to prevent or inhibit spoilage of a foodstuff by a microorganism. Preferably said microorganism is a bacterium (preferably a food-spoiling species from the *Pseudomonas* or *Bacillus* genera) or a fungus (preferably a food-spoiling species from one of the following genera: *Alternaria, Aspergillus, Fusarium, Botrytis, Colletotrichum, Saccharomyces, Kluyveromyces* and *Zygosaccharomyces*).

In preferred embodiments the foodstuff is derived from, provides, or is, a fruit, a nut, a vegetable, a seed, a sugar, a dairy product, a liquid or paste food, meat, fish or bread.

In preferred embodiments the foodstuff is a strawberry, preferably wherein the microorganism is *Botrytis cinerea* or *Colletotrichum acutatum*, preferably *Botrytis cinerea*.

In preferred embodiments said composition further comprises a chelating agent.

The inventors also provide a method of preventing or inhibiting spoilage of a foodstuff by a microorganism comprising administering to a foodstuff in need thereof an effective amount of a composition comprising an antimicrobial polypeptide comprising Blad or an active variant thereof.

DESCRIPTION OF THE DRAWINGS

The invention will be described with reference to the accompanying drawings, in which:

FIG. 1 shows the *Lupinus albus* β-conglutin precursor encoding sequence (SEQ ID NO: 1); and FIG. 2 shows the internal fragment of the β-conglutin precursor encoding sequence that corresponds to Blad (SEQ ID NO: 3).

DETAILED DESCRIPTION OF THE INVENTION

Blad

Blad ("banda de *Lupinus albus* doce"—band from sweet *L. albus*) was the name given to a stable and intermediary breakdown product of β-conglutin, the major storage protein present in seeds of the *Lupinus* genus. It was characterised as a 20 kD polypeptide, composed of 173 amino acid residues, and encoded by an internal fragment (519 nucleotides, deposited in GenBank under the accession number ABB13526) of the gene encoding the precursor of β-conglutin from *Lupinus* (1791 nucleotides, published in GenBank, under the accession number AAS97865). When primers encoding Blad terminal sequences are used to amplify a sequence from genomic *Lupinus* DNA, a ~620 bp product is obtained, indicating the presence of an intron in the gene fragment encoding Blad. Naturally-occurring Blad is the main component of a 210 kD glycooligomer which accumulates exclusively (following intensive limited proteolysis of β-conglutin) in the cotyledons of *Lupinus* species, between days 4 and 12 after the onset of germination. Whilst said oligomer is glycosylated, naturally-occurring Blad is non-glycosylated. The Blad-containing glycooligomer is composed of several polypeptides, the major ones exhibiting molecular masses of 14, 17, 20, 32, 36, 48 and 50 kD. The 20 kD polypeptide, Blad, is by far the most abundant polypeptide within the oligomer and appears to be the only one with lectin activity. Naturally-occurring Blad constitutes approximately 80% of the total cotyledonary protein in 8-day old plantlets.

The *L. albus* β-conglutin precursor encoding sequence (SEQ ID NO: 1) is given in FIG. 1. The β-conglutin parent subunit coding sequence is located at residues 70 to 1668. The encoded, 533 amino acid residue β-conglutin parent subunit (SEQ ID NO: 2) is:

MGKMRVRFPTLVLVLGIVFLMAVSIGIAYGEKDVLKSHERPEEREQEEW

QPRRQRPQSRREEREQEQEQGSPSYPRRQSGYERRQYHERSEQREEREQ

EQQQGSPSYSRRQRNPYHFSSQRFQTLYKNRNGKIRVLERFDQRTNRLE

NLQNYRIVEFQSKPNTLILPKHSDADYVLVVLNGRATITIVNPDRRQAY

NLEYGDALRIPAGSTSYILNPDDNQKLRVVKLAIPINNPGYFYDFYPSS

TKDQQSYFSGFSRNTLEATFNTRYEEIQRIILGNEDEQEYEEQRRGQEQ

SDQDEGVIVIVSKKQIQKLTKHAQSSSGKDKPSDSGPFNLRSNEPIYSN

KYGNFYEITPDRNPQVQDLNISLTYIKINEGALLLPHYNSKAIYVVVVD

EGEGNYELVGIRDQQRQQDEQEEKEEEVIRYSARLSEGDIFVIPAGYPI

SINASSNLRLLGFGINADENQRNFLAGSKDNVIRQLDRAVNELTFPGSA

EDIERLIKNQQQSYFANGQPQQQQQQQSEKEGRRGRRGSSLPF

The internal fragment of the β-conglutin precursor encoding sequence that corresponds to Blad (SEQ ID NO: 3) is given in FIG. 2. The Blad polypeptide (SEQ ID NO: 4) is:

RRQRNPYHFSSQRFQTLYKNRNGKIRVLERFDQRTNRLENLQNYRIVEF

QSKPNTLILPKHSDADYVLVVLNGRATITIVNPDRRQAYNLEYGDALRI

PAGSTSYILNPDDNQKLRVVKLAIPINNPGYFYDFYPSSTKDQQSYFSG

FSRNTLEATFNTRYEEIQRIILGNED

The invention relates to a composition comprising an antimicrobial polypeptide comprising Blad or an active variant thereof. It therefore relates to a composition comprising an antimicrobial polypeptide comprising the polypeptide sequence of SEQ ID NO: 4 or an active variant thereof. In alternative embodiments, the composition consists essentially of an antimicrobial polypeptide comprising Blad or an active variant thereof and/or the antimicrobial polypeptide consists essentially of Blad or an active variant thereof. In further embodiments the antimicrobial polypeptide comprising (or consisting essentially of) Blad or an active variant thereof may be used in isolated form.

An active variant of Blad is a variant of Blad that retains the ability to act as an antimicrobial (i.e. has antimicrobial activity—see below for a description of the level of such activity and how to measure it). "An active variant of Blad" includes within its scope a fragment of SEQ ID NO: 4. In preferred embodiments, a fragment of SEQ ID NO: 4 is selected that is at least 10% of the length of SEQ NO: 4, preferably at least 20%, preferably at least 30%, preferably at least 40%, preferably at least 50%, preferably at least 60%, preferably at least 70%, preferably at least 80%, preferably at least 90% and most preferably at least 95% of the length of SEQ NO: 4. Blad or a variant thereof generally has a length of at least 10 amino acid residues, such as at least 20, 25, 30, 40, 50, 60, 80, 100, 120, 140, 160 or 173 amino acid residues.

"An active variant of Blad" also includes within its scope a polypeptide sequence that has homology with SEQ ID NO: 4, such as at least 40% identity, preferably at least 60%, preferably at least 70%, preferably at least 80%, preferably at least 85%, preferably at least 90%, preferably at least 95%, preferably at least 97%, and most preferably at least 99% identity, for example over the full sequence or over a region of at least 20, preferably at least 30, preferably at least 40, preferably at least 50, preferably at least 60, preferably at least 80, preferably at least 100, preferably at least 120, preferably at least 140, and most preferably at least 160 or more contiguous amino acid residues. Methods of measuring protein homology are well known in the art and it will be understood by those of skill in the art that in the present context, homology is calculated on the basis of amino acid identity (sometimes referred to as "hard homology").

The homologous active Blad variant typically differs from the polypeptide sequence of SEQ ID NO: 4 by substitution, insertion or deletion, for example from 1, 2, 3, 4, 5 to 8 or more substitutions, deletions or insertions. The substitutions are preferably 'conservative', that is to say that an amino acid may be substituted with a similar amino acid, whereby similar amino acids share one of the following groups: aromatic residues (F/H/W/Y), non-polar aliphatic residues (G/A/P/I/L/V), polar-uncharged aliphatics (C/S/T/M/N/Q) and polar-charged aliphatics (D/E/K/R). Preferred sub-groups comprise: G/A/P; I/L/V; C/S/T/M; N/Q; D/E; and K/R.

An antimicrobial polypeptide comprising Blad or an active variant thereof (as described above) may consist of Blad or an active variant thereof with any number of amino acid residues added to the N-terminus and/or the C-terminus provided that the polypeptide retains antimicrobial activity (again, see below for a description of the level of such activity and how to measure it). Preferably, no more than 300 amino acid residues are added to either or both ends of Blad or an active variant thereof, more preferably no more than 200 amino acid residues, preferably no more than 150 amino acid residues, preferably no more than 100 amino acid residues, preferably no more than 80, 60 or 40 amino acid residues, most preferably no more than 20 amino acid residues.

An antimicrobial polypeptide comprising (or consisting essentially of) Blad or an active variant thereof (as described above) may be utilised in the invention in the form of a purified (e.g. removed from a plant, animal or microbial source) and/or recombinant protein. Production of a recombinant form enables the production of active variants of Blad.

Methods of purifying naturally-occurring Blad are already described in the art (e.g. Ramos et at (1997) Planta 203(1):

26-34 and Monteiro et at (2010) PLoS ONE 5(1): e8542). A suitable source of naturally-occurring Blad is a plant of the *Lupinus* genus, such as *Lupinus albus*, preferably a cotyledon of said plant, preferably harvested between about 4 to about 14 days after the onset of germination, more preferably harvested 6 to 12 days after the onset of germination (such as 8 days after the onset of germination). Methods are disclosed in the art for a total protein extraction leading to a crude extract comprising Blad, and for a protein purification of such an extract leading to a partially purified extract e.g. comprising the Blad-containing glycooligomer that comprises Blad.

To isolate Blad itself one can then use SDS-PAGE and/or, preferably, reverse phase (RP)-HPLC on a C-18 column.

An alternative way of obtaining a partially purified extract comprising the glycooligomer that comprises Blad is to utilise the chitin binding activity of Blad. The glycooligomer binds in a very strong manner to a chitin column as part of a chitin affinity chromatography purification, being eluted with 0.05 N HCl. Details of an example of this purification method are as follows:

Cotyledons from eight-day old lupin plants were harvested and homogenized in Milli-Q plus water (pH adjusted to 8.0), containing 10 mM $CaCl_2$ and 10 mM $MgCl_2$. The homogenate was filtered through cheesecloth and centrifuged at 30,000 g for 1 h at 4° C. The pellet was subsequently suspended in 100 mM Tris-HCl buffer, pH 7.5, containing 10% (w/v) NaCl, 10 mM EDTA and 10 mM EGTA, agitated for 1 h at 4° C., and centrifuged at 30,000 g for 1 h at 4° C. The total globulin fraction, contained in the supernatant, was precipitated with ammonium sulphate (561 g/l), left stirring in the cold for 1 h and centrifuged at 30,000 g for 30 min at 4° C. The pellet obtained was dissolved in 50 mM Tris-HCl buffer, pH 7.5, desalted in PD-10 columns equilibrated in the same buffer and passed through a chitin-affinity chromatography column pre-equilibrated in the same buffer. The column was washed with 50 mM Tris-HCl buffer, pH 7.5, and the bound proteins eluted with 0.05 N HCl. The eluted fractions were immediately neutralized with 2 M Tris and the peak fractions pooled, lyophilized and analyzed by SDS-PAGE.

For the preparation of the chitin column, crude chitin was obtained from Sigma and processed as follows: the chitin sample was washed extensively with Milli-Q plus water, followed by 0.05 N HCl. It was then washed with 1% (w/v) sodium carbonate and then with ethanol, until the absorbance of the wash was less than 0.05. Chitin was then packed into a pipette tip and equilibrated with 50 mM Tris-HCl buffer, pH 7.5.

Methods of producing recombinant proteins are well known in the art. Such methods as applied here will involve inserting the polynucleotide encoding a polypeptide comprising Blad or an active variant thereof into a suitable expression vector—enabling the juxtaposition of said polynucleotide with one or more promoters (e.g. an inducible promoter, such as T7lac) and with other polynucleotides or genes of interest—introducing the expression vector into a suitable cell or organism (e.g. *Escherichia coli*), expressing the polypeptide in the transformed cell or organism and removing the expressed recombinant polypeptide from that cell or organism. To assist such purification the expression vector may be constructed such that the polynucleotide additionally encodes, for example, a terminal tag that can assist purification: e.g., a tag of histidine residues for affinity purification. Once the recombinant polypeptide is purified, the purification tag may be removed from the polypeptide, e.g., by proteolytic cleavage.

In a composition comprising an antimicrobial polypeptide comprising (or consisting essentially of) Blad or an active variant thereof, said polypeptide is preferably in partially purified form, more preferably in purified form. Said polypeptide is partially purified when it is present in an environment lacking one or more other polypeptides with which it is naturally associated and/or is represented by at least about 10% of the total protein present. Said polypeptide is purified when it is present in an environment lacking all, or most, other polypeptides with which it is naturally associated. For example, purified Blad means that Blad represents at least about 50%, at least about 60%, at least about 70%, at least about 75%, at least about 80%, at least about 85%, at least about 90%, at least about 95%, at least about 97%, at least about 98%, or at least about 99% of the total protein in a composition.

In a composition comprising an antimicrobial polypeptide comprising (or consisting essentially of) Blad or an active variant thereof, the *Lupinus* protein content may consist essentially of the Blad-containing glycooligomer that comprises a polypeptide that comprises (or consist essentially of) Blad or an active variant thereof.

A composition comprising an antimicrobial polypeptide comprising (or consisting essentially of) Blad may also be a formulation comprising another compound(s) added to the composition by the skilled person.

Food Spoilage and Foodstuffs

Spoilage of a foodstuff by a microorganism means any alteration of a foodstuff by a microorganism that results in a change in e.g. the taste, odour or appearance (e.g. shape, colour, texture, firmness) that decreases its nutritional and/or commercial value. By foodstuff it is intended to mean any liquid or solid substance intended for consumption by a human or animal for nutritional or pleasurable reasons. The foodstuff may be consumed directly or indirectly (e.g. after cooking or processing, such as refinement of cereals). Where applicable, the foodstuff is preferably contemplated in a form isolated from its natural environment, such as harvested plant foodstuffs (e.g. fruit, vegetables, seeds) and products isolated from animals (e.g. meat, fish, milk).

The foodstuff may be derived from, may provide, or may be, a fruit, a nut, a vegetable, a seed, a sugar, a dairy product, a liquid or paste food, meat, fish or bread. Foodstuffs derived from fruit include wine and fruit juice. Plants providing seeds include cereals (e.g. maize, wheat, barley, sorghum, millet, rice, oats and rye) and legumes (e.g. beans, peas and lentils). Sugars, preferably sucrose, may be derived from sugar beet or sugar cane. Dairy products include milk, cream, cheese and yoghurt. Liquid or paste food includes soup, sauces, pickles, mayonnaise, salad cream and other salad dressings, preserves, syrup and baby food. The meat and/or fish foodstuffs contemplated may be processed or otherwise, and may be cooked or otherwise. Further particular foodstuffs that are contemplated may be found in the next section, which refers to example foodstuffs that may be spoiled by microorganisms which may be targeted in the uses and methods of the invention.

Foodstuffs also include pre-prepared composite foods such as sandwiches, pies, quiches etc, especially those currently designed for chilled storage.

Microbial Targets

The inventors provide the use of a composition comprising an antimicrobial polypeptide comprising Blad or an active variant thereof to prevent or inhibit spoilage of a foodstuff by a microorganism. Microorganisms that may cause spoilage of a foodstuff—food-spoiling microorganisms—include, in particular, bacteria and fungi. In such use the antimicrobial polypeptide may be considered as an antimicrobial food preservative.

The antimicrobial polypeptide can be used to prevent or inhibit food spoilage by either Gram-positive or Gram-negative bacteria. Particularly preferred bacterial targets (with examples of foodstuffs that they may spoil given in brackets) include: food-spoiling *Pseudomonas* species, such as *Pseudomonas aeruginosa* (thale cress and lettuce), *Pseudomonas syringae* (various plant-derived foodstuffs such as beet, wheat and barley), *Pseudomonas tolaasii* (mushroom), *Pseudomonas agarici* (mushroom), *Pseudomonas fragi* (dairy products) and *Pseudomonas lundensis* (milk, cheese, meat and fish), most preferably *P. aeruginosa*; and food-spoiling *Bacillus* species such as *Bacillus subtilis* (tomato, potato, bread) and *Bacillus coagulans* (milk, tomato juice).

The antimicrobial polypeptide can be used to prevent or inhibit food spoilage by either unicellular (yeast) or multicellular (filamentous, mold) fungi. Particularly preferred yeast targets (with examples of foodstuffs that they may spoil given in brackets) include: food-spoiling *Saccharomyces* species, such as *Saccharomyces cerevisiae* (sugar, sugar syrups, wine, and soft drinks such as fruit juices); food-spoiling *Kluyveromyces* species, such as *Kluyveromyces marxianus* (cheese); and food-spoiling *Zygosaccharomyces* species, such as *Zygosaccharomyces bailii* (wine, fruit juice, salad dressings and tomato sauce) and *Zygosaccharomyces rouxii* (sugar syrups, fruit juices, jams and salad dressings). Particularly preferred mold targets (with examples of foodstuffs that they may spoil given in brackets) include: food-spoiling *Alternaria* species, such as *Alternaria alternate* (potato), *Alternaria arborescens* (tomato), *Alternaria arbusti* (Asian pear), *Alternaria brassicae* (vegetables), *Alternaria brassicicola* (cole crops), *Alternaria carotiincultae* (carrot), *Alternaria conjuncta* (parsnip), *Alternaria dauci* (carrot), *Alternaria euphorbiicola* (cole crops), *Alternaria gaisen* (pear), *Alternaria infectoria* (wheat), *Alternaria japonica* (cole crops), *Alternaria petroselini* (parsley), *Alternaria selini* (parsley), *Alternaria solani* (potato, tomato) and *Alternaria smyrnii* (alexanders, parsley); food-spoiling *Aspergillus* species, such as *Aspergillus fumigatus* (nuts, potato, rice and bread), *Aspergillus niger* (fruit and vegetables e.g. grapes and onions), and *Aspergillus flavus* (corn, peanut); food-spoiling *Fusarium* species, such as *Fusarium oxysporum* (fruit) and *Fusarium graminearum* (barley, wheat and maize); food-spoiling *Botrytis* species, such as *Botrytis cinerea* (strawberry, grape and tomato); and food-spoiling *Colletotrichum* species, such as *Colletotrichum actuatum* (strawberry, celery, apple, avacado, aubergine, coffee and guava), *Colletotrichum coccodes* (tomato, potato), *Colletotrichum capsici* (basil, chickpea, pepper), *Colletotrichum crassipes* (passion fruit), *Colletotrichum gloeosporioides* (vegetables and fruit e.g. quince and apple), *Colletotrichum graminicola* (cereals), *Colletotrichum kahawae* (coffee), *Colletotrichum lindemuthianum* (bean), *Colletotrichum musae* (banana), *Colletotrichum nigrum* (tomato), *Colletotrichum orbiculare* (melon, cucumber), *Colletotrichum pisi* (pea) and *Colletotrichum sublineolum* (rice).

In preferred embodiments the antimicrobial polypeptide is used to prevent or inhibit spoilage of a fruit by a microorganism, preferably a strawberry, and preferably wherein the microorganism is *Botrytis cinerea* or *Colletotrichum acutatum*, preferably *Botrytis cinerea*.

The skilled person will be able to identify, through routine methods, a suitable concentration (i.e. an effective concentration) with which to use the antimicrobial polypeptide to prevent or inhibit spoilage in any particular setting. Preferably, for example, Blad is used at a concentration of at least 1 µg/ml, at least 5 µg/ml, at least 10 µg/ml, at least 50 µg/ml, at least 100 µg/ml, or at least 150 µg/ml, and up to 350 µg/ml, up to 500 µg/ml, up to 600 µg/ml, up to 1 mg/ml, up to 2.5 mg/ml, up to 5 mg/ml or up to 10 mg/ml. Preferably the concentration of Blad selected is between 10 µg/ml and 5 mg/ml, more preferably between 50 µg/ml and 2.5 mg/ml, more preferably between 100 µg/ml and 1 mg/ml, and even more preferably between 150 µg/ml and 600 µg/ml (such as about 250 µg/ml). The inventors have provided evidence (see Examples 4 and 5) that Blad is non-toxic to animals to at least 400 µg/ml.

The inventors have surprisingly found that a combination of Blad with a chelating agent (e.g. EDTA) produces a synergistic antimicrobial effect. Therefore, preferably, a chelating agent is used to improve the antimicrobial activity of the antimicrobial polypeptide, and the use of such a chelating agent may decrease the concentration of the antimicrobial polypeptide required to achieve a particular level of prevention or inhibition of spoilage. A chelating agent (also known as a chelant, a chelator or a sequestering agent) is any compound that binds to a metal ion to form a non-covalent complex and reduces the ion's activity. Suitable chelating agents include polyamino carboxylates, such as EDTA (ethylenediaminetetraacetic acid) and EGTA (ethyleneglycol bis($\beta$-aminoethyl ether)-N,N,N',N'-tetraacetic acid). Preferably, EDTA is used as the chelating agent, preferably at a concentration of at least 10 µg/ml, at least 50 µg/ml, or at least 100 µg/ml, and up to 500 µg/ml, up to 1 mg/ml, up to 5 mg/ml, up to 10 mg/ml, or up to 20 mg/ml. Preferably, EDTA is used at a concentration of between 0.1 mg/ml and 1 mg/ml.

Outcomes

The antimicrobial polypeptide may be used to inhibit the growth of a food-spoiling microorganism (meaning that it has microbistatic activity) and/or to kill said microorganism (meaning that it has microbicidal activity) on a foodstuff such that spoilage of said foodstuff by said microorganism is prevented or inhibited. The skilled person will be able to identify a suitable dose and/or concentration to obtain a particularly desired growth inhibition or killing of the microorganism.

Preferably, when used as a microbistatic agent, the antimicrobial polypeptide reduces the rate of growth by 10%, more preferably by 50%, more preferably by 75%, more preferably by 90%, more preferably by 95%, more preferably by 98%, more preferably by 99%, and even more preferably by 99.9% in comparison to equivalent conditions where the antimicrobial polypeptide is not present. Most preferably the antimicrobial polypeptide prevents any growth of the microorganism.

Preferably, when used as a microbicidal agent, the antimicrobial polypeptide kills 10% of the population of the microorganims, more preferably 50% of said population, more preferably 75% of said population, more preferably 90% of said population, more preferably 95% of said population, more preferably 98% of said population, more preferably 99% of said population, and even more preferably by 99.9% of said population in comparison to equivalent conditions where the antimicrobial polypeptide is not present. Most preferably the antimicrobial polypeptide kills all of the population of the microorganism.

When used to prevent or inhibit spoilage of a foodstuff by a microorganism the antimicrobial polypeptide is preferably used in an effective amount, that is to say an amount that provides a level of growth inhibition and/or killing of a microorganism such that a detectable level of spoilage prevention or inhibition (e.g. a decrease in the rate of spoilage) is achieved, preferably in comparison to equivalent conditions where the antimicrobial polypeptide is not present. Preferably, the effective amount of the antimicrobial polypeptide is non-toxic to a human or animal.

Uses and Methods

The inventors provide the use of a composition comprising an antimicrobial polypeptide comprising Blad or an active variant thereof to prevent or inhibit spoilage of a foodstuff by a microorganism. To this end they also provide a method of preventing or inhibiting spoilage of a foodstuff by a microorganism comprising administering to a foodstuff in need thereof an effective amount of a composition comprising an antimicrobial polypeptide comprising Blad or an active variant thereof. Preferably, the effective amount of the antimicrobial polypeptide is non-toxic to humans or animals. The prevention or inhibition of spoilage can occur during the storage, transport, handling, processing or display of the foodstuff.

A composition comprising the antimicrobial polypeptide can for example be mixed into the foodstuff or may for example be applied to the surface of the foodstuff (for example as a liquid film or a spray). The foodstuff may also be immersed in (and optionally maintained in) said composition. For any particular foodstuff the use of said composition as a preservative can be combined with any other well known food preservation technique, antimicrobial or otherwise, including drying, heating, refrigerating or freezing, osmotic inhibition (e.g. use of syrups or salt), vacuum packing, canning and bottling, jellying, potting, jugging, ionising irradiation, pulsed electric field processing, high pressure food preservation, and ultra high water pressure food preservation, use of antioxidants, and/or use of other antimicrobial preservatives (e.g. sulphur dioxide, carbon dioxide, ethanol, acetic acid, citric acid, lactic acid, sorbic acid, benzoates nitrates and nitrites, sulphites, calcium propionate and methylchloroisothiazolinone).

EXAMPLES

In the following Examples BLAD denotes the naturally-occurring Blad-containing glycooligomer comprising the 20 kD Blad polypeptide, purified as per Ramos et at (1997) Planta 203(1): 26-34: see "Plant material and growth conditions" and "Purification of proteins" parts of the Materials and Methods section of that document.

DEFINITIONS

MIC—Minimum Inhibitory Concentration: the lowest concentration of an antimicrobial that inhibits the visible growth of a microorganism.

MFC/MBC—Minimum Fungicidal/Bactericidal Concentration (or Minimal Lethal Concentration): the lowest concentration of an antimicrobial agent needed to kill 99.9% of the initial inoculum after 24 hours under a standardized set of conditions.

Example 1

Bactericidal Activity of BLAD

MIC and MBC of BLAD for Various Bacterial Species (Using Mueller-Hinton Medium):

| Bacterial Species | MIC (µg/ml) | MBC (µg/ml) |
|---|---|---|
| *Pseudomonas aeruginosa* | 32-256 | 128-256 |
| *Listeria monocytogenes* | 8 | >512 |
| *Bacillus subtilis* | 4 | >512 |
| *Staphylococcus aureus* | 8 | >512 |
| *Salmonella thyphimurium* | 64 | 128 |

In particular, *P. aeruginosa* and *B. subtilis* can cause food spoilage. BLAD was found to be bacteriostatic at 100 µg/ml and bactericidal at 250 µg/ml against *P. aeruginosa*. Against *P. aeruginosa* BLAD at 50 µg/ml or EDTA at 1 mg/ml inhibits growth (i.e. both are bacteriostatic) but a combination of the two is bactericidal.

Example 2

Fungicidal Activity of BLAD

MIC and MFC of BLAD for Various Filamentous Fungi (Using RPMI Medium)

| Fungal Species | MIC (µg/ml) | MFC (µg/ml) |
|---|---|---|
| *Alternaria* sp. | 64 | >512 |
| *Aspergillus fumigatus* | 32 | >512 |
| *Aspergillus niger* | 32-64 | >512 |
| *Botrytis cinerea* | 128 | 512 |
| *Colletotrichum acutatum* | 64 | >512 |
| *Colletotrichum gloesporioides* | 64 | >512 |
| *Fusarium oxysporum* | 64 | >512 |

MIC of BLAD for Various Filamentous Fungi (Using Various Media):

| | MIC (µg/ml) | | | |
|---|---|---|---|---|
| Strain | PDB | PDB pH 7.5 | AM3 | RPMI |
| *Botrytis cinerea* BM | 128 (1) | 4-8 (3) | 8-32 (3) | 128 (2) |
| *B. cinerea* BT | 32-128 (3) | 8 (3) | 16-32 (3) | 64-128 (3) |
| *Colletotrichum kahawae* (from Kenya) | 32 | 4 | 1-4 | 64 |
| *C. kahawae* (from Zimbabwe) | 16 | 4-8 | 4-16 | 64 |

Inhibition Halo (Diameter) Data for BLAD Against *Botrytis cinera* BM on Potato Dextrose Agar (PDA) at 0.6% or 0.9% w/v (Incubation 3 Days at 25° C.):

| BLAD per disk (µg) | Average halo diameter on 0.6% agar (mm) | Average halo diameter on 0.9% agar (mm) |
|---|---|---|
| 20 µg | 0 | 0 |
| 50 µg | 13 | 0 |
| 100 µg | 25.5 | 11 |
| 200 µg | 36 | 22 |

On 0.6% agar, growth of *B. cinera* was increasingly inhibited with increasing amounts of BLAD from 20 µgl to 200 µg. A less marked inhibition was seen at 5 mg/ml and 10 mg/ml on 0.9% agar.

Inhibition Halo (Diameter) Data for BLAD at 200 µg/Disk Against Various Yeasts on PDA with 0.9% (w/v) Agar (Incubation 3 to 5 Days Days at 25° C.):

| Yeast | Average inhibition halo diameter (mm) |
|---|---|
| *Saccharomyces cerevisiae* | 30 |
| *Kluyveromyces marxianus* | 28 |
| *Zygosaccharomyces bailii* | >40 |
| *Zygosaccharomyces rouxii* | 40 |

BLAD at 200 µg/disk showed significant growth inhibition of all of these yeasts, all of which can cause food spoilage.

Example 3

Strawberry Preservation/Decontamination Assays

The susceptibility of strawberries to *B. cinerea* contamination following treatment with BLAD was investigated. Up to 38% of untreated strawberries supplied by a commercial supplier were found to be contaminated (sample size: ten 500 g boxes), underlining the problem of strawberry contamination.

Assay Protocol

1. Prepare homogeneous and representative samples.
2. Wash in water and decontaminate using 70% v/v ethanol.
3. Rinse twice in water.
4. Treat with BLAD at various concentrations (omitted for control): immerse in treatment solution for 1 minute before leaving to dry in incubation petri dishes (containing a wet sponge housing sterile water, filter paper and plastic mesh).
6. Innoculate each strawberry with 10 µl of *B. cinerea* spore solution at $1-5 \times 10^6$ spores/ml.
7. Incubate for 5 days under the following conditions:
   Temperature: 25° C. (+/−3° C.)
   Relative humidity: 80-90%
   Lighting: protected from direct sunlight
8. At intervals, collect 1 g sample and homogenize using a vortex.
9. Perform serial decimal dilution.
10. Disperse on solid media and perform colony count.

All handling techniques were performed under sterile conditions, using autoclaved material.

The following data represent the percentage of strawberries infected with *B. cinerea* after inoculation with the *B. cinerea* spore solution:

| Days post inoculation | BLAD concentration (mg/ml): | | | | |
|---|---|---|---|---|---|
| | 0(control) | 50 | 150 | 250 | 350 |
| 0 | 0 | 0 | 0 | 0 | 0 |
| 1 | 44 | 33 | 4 | 0 | 0 |
| 2 | 63 | 63 | 15 | 6 | 5 |
| 3 | 93 | 77 | 46 | 50 | 40 |
| 4 | 100 | 100 | 56 | 70 | 60 |
| 5 | 100 | 100 | 73 | 70 | 64 |

BLAD at concentrations of 150 µg/ml to 350 µg/ml significantly delayed the onset of contamination with *B. cinerea* and reduced the total proportion of contaminated strawberries in comparison to the control.

Example 4

Dermal Toxicity Study of BLAD in Guinea Pigs

Confidential study carried out at the Faculty of Veterinary Medicine, Technical University of Lisbon, on behalf of Instituto Superior de Agronomia (Jul. 18, 2006-Aug. 1, 2006) using OECD Guideline for testing of chemicals, No. 402, Acute Dermal Toxicity. The study was conducted in accordance with good laboratory practice and animal welfare.

The acute dermal toxicity of BLAD was evaluated after single dose exposure in guinea pigs, which are widely accepted as suitable animals for dermal toxicity studies. BLAD was applied to the glabrous skin in two groups of 10 animals each, with dosing at 200 µg/ml and 400 µg/ml respectively. After exposure the animals were kept under observation for a period of 15 days, during which body mass, morbidity and mortality were recorded.

Materials and Methods

1. Materials

Test item: BLAD was supplied at 5 mg/ml (yellowish opaque liquid, 0-4° C.) and stored at −80° C.

Animals: albino guinea pigs; strain: Dunkin Hartley (Hsd-Poc: DH) by Harlan Iberica, Barcelona.

Number of animals used: 30.

Body weight: 400-449 g.

Age: 6 weeks.

Lodging: the animals were individually placed in polyethylene boxes with sterilized wood shavings (Lignocel).

Ambient conditions:

a) Photoperiod: cycles of light/dark for 12 h in 12 h.

b) Controlled environment: an average temperature of 19/22° C. and average humidity of 60%.

Adaptation: the animals were kept under environmental conditions of the test for seven days before the start of the test.

Food: Global Diet 2014, Rodent Maintenance Diet supplied by Harlan Iberica, Barcelona; water ad libitum.

2. Methods

Administration: animals were shaved 48 h before the test and only animals that had lesion-free skin were taken forward in the study. An aliquot of 1 ml (at either 200 µg/ml or 400 µg/ml) was applied to the shaved skin of each animal.

Study design: the 30 animals of the study were divided into four groups, two groups of ten animals each and two groups with five animals each. A group of ten animals was exposed to BLAD at 200 µg/ml (test group 1) and another group of ten animals was exposed to BLAD at 400 µg/ml (test group 2). The two groups of five animals served as controls: one group was exposed to water (1 ml aliquot) whilst another group was not subjected to any administration but handled as per all the other groups.

Outcomes: after exposure the animals were observed daily for 15 days to record any signs of morbidity or even death. In terms of morbidity particular attention was paid to possible appearance of skin lesions at the site of exposure and possible signs of general toxicity such as changes in normal behavior patterns. Body weight was individually assessed before exposure and at the end of test period.

Results

At neither concentration of BLAD were there signs of any physical changes in the dermal administration area or changes in drinking/feeding or general behavior. No adverse reactions or death occurred upon BLAD administration.

Increase in body mass was similar in all groups (and was consistent with the increase expected from developing animals of such young age).

Conclusions

BLAD at concentrations up to 400 µg/ml (and possibly higher) does not show dermal toxicity.

Example 5

Oral Toxicity Study of BLAD in Albino Rats

Confidential study carried out at the Faculty of Veterinary Medicine, Technical University of Lisbon, on behalf of Instituto Superior de Agronomia, using OECD Guideline for testing of chemicals, No. 401, Acute Oral Toxicity. The study was conducted in accordance with good laboratory practice and animal welfare.

The acute oral toxicity of BLAD was evaluated after single dose exposure in rats, which are widely accepted as suitable animals for acute oral toxicity studies. BLAD was administered by gavage in two groups of 10 animals each, with dosing at 200 µg/ml and 400 µg/ml respectively. After exposure the animals were kept under observation for a period of 15 days, during which body mass, morbidity and mortality were recorded. After the observation period the animals were euthanized and underwent necropsy.

Materials and Methods

1. Materials

Test item: BLAD was supplied at 5 mg/ml (yellowish opaque liquid, 0-4° C.) and stored at −80° C.

Animals: *Rattus norvegicus*, strain: Wistar Hannover, acquired by the vivarium of the Faculty of Veterinary Medicine of Lisbon from Harlan Iberica, Barcelona.

Number of animals used: 30.
Body weight: 250-300 g.
Age: 10 weeks.

Lodging: the animals were individually placed in polyethylene boxes with sterilized wood shavings (Lignocel).

Ambient conditions:
a) Photoperiod: cycles of light/dark for 12 h in 12 h.
b) Controlled environment: an average temperature of 19/22° C. and average humidity of 60%.

Adaptation: the animals were kept under environmental conditions of the test for seven days before the start of the test.

Food: Global Diet 2014, Rodent Maintenance Diet supplied by Harlan Iberica, Barcelona; water ad libitum.

2. Methods

Administration: an aliquot of 1 ml (at either 200 µg/ml or 400 µg/ml) was applied to each animal by oral (oro-esophageal) intubation, commonly known as gavage. The administration was carried out with a metal probe appropriate to the species of animal used. The animals were subjected to fasting for 18 h prior to administration and fed 3 h following administration.

Study design: the 30 animals of the study were divided into four groups, two groups of ten animals each and two groups with five animals each. A group of ten animals was exposed to BLAD at 200 µg/ml (test group 1) and another group of ten animals was exposed to BLAD at 400 µg/ml (test group 2). The two groups of five animals served as controls: one group was exposed to water (1 ml aliquot) whilst another group was not subjected to any administration but handled as per all the other groups.

Outcomes: after administration the animals were observed daily for 15 days to record any signs of morbidity or even death. Body weight was individually assessed before exposure and at the end of test period. After the observation period the animals were euthanized (by asphyxiation in an atmosphere saturated with carbon dioxide) for subsequent post-mortem examination.

Results

At neither concentration of BLAD were there signs of any physical changes or changes in drinking/feeding or general behavior. No adverse reactions or death occurred upon BLAD administration. Increase in body mass was similar in all groups (and was consistent with the increase expected from developing animals of such young age). Necropsy/macroscopic observation of the organs of the thoracic and abdominal cavity revealed no changes thereto.

Conclusions

BLAD at concentrations up to 400 µg/ml (and possibly higher) does not show oral toxicity.

The invention claimed is:

1. A method of inhibiting spoilage of foodstuffs by a microorganism comprising administering to a foodstuff in need thereof an effective amount of a composition comprising an antimicrobial polypeptide comprising SEQ ID NO:4 or an active variant thereof which has antimicrobial activity which comprises a sequence which has at least 85% identity to either SEQ ID NO:4 or to a fragment of SEQ ID NO:4 which is at least 100 amino acids in length, and in the case where the foodstuff is a plant foodstuff it is a harvested foodstuff, and said inhibiting of spoilage occurs during storage, transport, handling, processing or display of the foodstuff.

2. The method according to claim 1 wherein the microorganism is a fungus.

3. The method according to claim 2 wherein the fungus is a food-spoiling species of a genera selected from the group consisting of: *Alternaria, Aspergillus, Fusarium, Botrytis, Collectotrichum, Saccharomyces, Kluyveromyces* and *Zygosaccharomyces*.

4. The method according to claim 1 wherein the foodstuff is derived from, provides, or is, a fruit, a nut, a vegetable, a seed, a sugar, a dairy product, a liquid or paste food, meat, fish or bread.

5. The method according to claim 1 wherein the foodstuff is a strawberry.

6. The method according to claim 1 wherein the microorganism is *Botrytis cinerea* or *Colletotrichum acutatum*.

7. The method according to claim 1 wherein said composition further comprises a chelating agent.

* * * * *

SEQUENCE LISTING

```
<160> NUMBER OF SEQ ID NOS: 4

<210> SEQ ID NO 1
<211> LENGTH: 1791
<212> TYPE: DNA
<213> ORGANISM: Lupinus albus

<400> SEQUENCE: 1
gatggcgatg aatgaacact gcgtttgctg gctttgatga aaatcgagtg caacctaata      60
taatcaaata tgggtaagat gagagtgagg tttccaacgt tagtgttggt actaggaata     120
gtattcctca tggcagtgtc aattggtatt gcttatggag aaaaagatgt gctaaagagt     180
catgagaggc ctgaggaaag agaacaagag gagtggcaac ctaggagaca acgacctcaa     240
agtagaaggg aagagagaga gcaagagcaa gagcagggtt ctccctcata cccacgcagg     300
cagagtggtt atgagaggag acaataccat gagaggagtg agcagaggga agagagagag     360
```

```
caagaacaac aacaaggttc tccctcatac tcacgtagac aaaggaaccc ttatcacttc    420
agctctcaaa gattccaaac tctttacaaa aataggaatg gcaaaatccg tgtgctcgag    480
aggtttgacc aaagaaccaa tagacttgag aatctccaaa actaccgcat tgttgagttc    540
caatcaaaac ctaacactct cattctccct aaacactctg atgctgacta cgtcctcgtt    600
gtactcaatg gtagagccac aatcacgata gtaaaccctg atagaagaca agcatataac    660
cttgagtatg gcgatgctct cagaatccca gctggctcaa cttcatatat ccttaacccg    720
gatgacaacc agaagcttag agtagtcaag ctcgcaatac ccatcaacaa tcctggctac    780 tttatgatt tctatccatc gagtactaaa gaccaacaat cctacttcag tggcttcagc    840
aggaacactt tagaggccac cttcaatact cgttatgaag agatacaaag gattatttta    900
gggaatgagg atgagcaaga atatgaggaa caaggcgtg ggcaagagca gagcgaccaa    960
gacgaggggg tgatagtgat agtttcaaag aaacagatcc aaaaattgac aaaacacgct   1020
caatcttcat caggaaaaga caaaccctct gattctggcc ccttcaactt gagaagcaat   1080
gagcccatat attcaaacaa gtatgggaac ttctatgaaa tcactccaga tagaaaccct   1140
caagttcagg atttgaatat ctctctcacc tatataaaaa ttaacgaggg agctttgttg   1200
ttgccacact ataactcaaa ggccatatat gtagtcgtgg ttgatgaagg agaaggaaat   1260
tatgaactgg taggtattcg agatcaacaa cgacaacaag atgagcaaga agagaaagag   1320
gaagaagtga taaggtatag tgctagatta tcagaaggtg acattttgt aattccagca   1380 ggttatccaa tttccatcaa tgcttcctca aatcttcgct tgcttggatt tggcatcaat   1440
gctgatgaaa accagaggaa tttcctcgca ggttctaaag acaatgtgat aaggcagtta   1500
gatagagcag tgaatgagct cacattccct ggttctgctg aagatattga gagattaatc   1560
aaaaaccaac aacagtctta ctttgcaaat ggtcagcctc aacaacaaca acaacaacaa   1620
agtgagaagg agggaaggcg tggaagaagg ggttcatctc ttccattttg agcactttt   1680 actaagctgt tttaaaagct actatcatgt aagagctcat agtgagctac tgagagaata   1740
ataaaactaa agttggacct ttgtactaat aatgttaata aaaaaaaaa a             1791
```

<210> SEQ ID NO 2
<211> LENGTH: 533
<212> TYPE: PRT
<213> ORGANISM: Lupinus albus

<400> SEQUENCE: 2

```
Met Gly Lys Met Arg Val Arg Phe Pro Thr Leu Val Leu Val Leu Gly
1               5                   10                  15

Ile Val Phe Leu Met Ala Val Ser Ile Gly Ile Ala Tyr Gly Glu Lys
            20                  25                  30

Asp Val Leu Lys Ser His Glu Arg Pro Glu Glu Arg Gln Glu Glu
        35                  40                  45

Trp Gln Pro Arg Arg Gln Arg Pro Gln Ser Arg Glu Glu Arg Glu
    50                  55                  60

Gln Glu Gln Glu Gln Gly Ser Pro Ser Tyr Pro Arg Arg Gln Ser Gly
65                  70                  75                  80

Tyr Glu Arg Arg Gln Tyr His Glu Arg Ser Gln Arg Glu Glu Arg
                85                  90                  95

Glu Gln Glu Gln Gln Gln Gly Ser Pro Ser Tyr Ser Arg Arg Gln Arg
            100                 105                 110

Asn Pro Tyr His Phe Ser Ser Gln Arg Phe Gln Thr Leu Tyr Lys Asn
```

```
            115                 120                 125
Arg Asn Gly Lys Ile Arg Val Leu Glu Arg Phe Asp Gln Arg Thr Asn
130                 135                 140
Arg Leu Glu Asn Leu Gln Asn Tyr Arg Ile Val Glu Phe Gln Ser Lys
145                 150                 155                 160
Pro Asn Thr Leu Ile Leu Pro Lys His Ser Asp Ala Asp Tyr Val Leu
                    165                 170                 175
Val Val Leu Asn Gly Arg Ala Thr Ile Thr Ile Val Asn Pro Asp Arg
                180                 185                 190
Arg Gln Ala Tyr Asn Leu Glu Tyr Gly Asp Ala Leu Arg Ile Pro Ala
                195                 200                 205
Gly Ser Thr Ser Tyr Ile Leu Asn Pro Asp Asp Asn Gln Lys Leu Arg
            210                 215                 220
Val Val Lys Leu Ala Ile Pro Ile Asn Asn Pro Gly Tyr Phe Tyr Asp
225                 230                 235                 240
Phe Tyr Pro Ser Ser Thr Lys Asp Gln Gln Ser Tyr Phe Ser Gly Phe
                    245                 250                 255
Ser Arg Asn Thr Leu Glu Ala Thr Phe Asn Thr Arg Tyr Glu Glu Ile
                260                 265                 270
Gln Arg Ile Ile Leu Gly Asn Glu Asp Glu Gln Glu Tyr Glu Glu Gln
            275                 280                 285
Arg Arg Gly Gln Glu Gln Ser Asp Gln Asp Glu Gly Val Ile Val Ile
290                 295                 300
Val Ser Lys Lys Gln Ile Gln Lys Leu Thr Lys His Ala Gln Ser Ser
305                 310                 315                 320
Ser Gly Lys Asp Lys Pro Ser Asp Ser Gly Pro Phe Asn Leu Arg Ser
                    325                 330                 335
Asn Glu Pro Ile Tyr Ser Asn Lys Tyr Gly Asn Phe Tyr Glu Ile Thr
                340                 345                 350
Pro Asp Arg Asn Pro Gln Val Gln Asp Leu Asn Ile Ser Leu Thr Tyr
            355                 360                 365
Ile Lys Ile Asn Glu Gly Ala Leu Leu Leu Pro His Tyr Asn Ser Lys
        370                 375                 380
Ala Ile Tyr Val Val Val Asp Glu Gly Glu Gly Asn Tyr Glu Leu
385                 390                 395                 400
Val Gly Ile Arg Asp Gln Gln Arg Gln Gln Asp Glu Gln Glu Glu Lys
                    405                 410                 415
Glu Glu Glu Val Ile Arg Tyr Ser Ala Arg Leu Ser Glu Gly Asp Ile
                420                 425                 430
Phe Val Ile Pro Ala Gly Tyr Pro Ile Ser Ile Asn Ala Ser Ser Asn
            435                 440                 445
Leu Arg Leu Leu Gly Phe Gly Ile Asn Ala Asp Glu Asn Gln Arg Asn
        450                 455                 460
Phe Leu Ala Gly Ser Lys Asp Asn Val Ile Arg Gln Leu Asp Arg Ala
465                 470                 475                 480
Val Asn Glu Leu Thr Phe Pro Gly Ser Ala Glu Asp Ile Glu Arg Leu
                    485                 490                 495
Ile Lys Asn Gln Gln Ser Tyr Phe Ala Asn Gly Gln Pro Gln Gln
                500                 505                 510
Gln Gln Gln Gln Gln Ser Glu Lys Glu Gly Arg Arg Gly Arg Arg Gly
            515                 520                 525
Ser Ser Leu Pro Phe
        530
```

```
<210> SEQ ID NO 3
<211> LENGTH: 519
<212> TYPE: DNA
<213> ORGANISM: Lupinus albus

<400> SEQUENCE: 3
cgtagacaaa ggaacccttu tcacttcagc tctcaaagat tccaaactct ttacaaaaat    60
aggaatggca aaatccgtgt gctcgagagg tttgaccaaa gaaccaatag acttgagaat   120
ctccaaaact accgcattgt tgagttccaa tcaaaaccta acactctcat tctccctaaa   180
cactctgatg ctgactacgt cctcgttgta ctcaatggta gagccacaat cacgatagta   240
aaccctgata gaagacaagc atataacctt gagtatggcg atgctctcag aatcccagct   300
ggctcaactt catatatcct taacccggat gacaaccaga agcttagagt agtcaagctc   360
gcaataccca tcaacaatcc tggctacttt tatgatttct atccatcgag tactaaagac   420
caacaatcct acttcagtgg cttcagcagg aacactttag aggccacctt caatactcgt   480
tatgaagaga tacaaaggat tattttaggg aatgaggat                          519

<210> SEQ ID NO 4
<211> LENGTH: 173
<212> TYPE: PRT
<213> ORGANISM: Lupinus albus

<400> SEQUENCE: 4

Arg Arg Gln Arg Asn Pro Tyr His Phe Ser Ser Gln Arg Phe Gln Thr
1               5                  10                  15

Leu Tyr Lys Asn Arg Asn Gly Lys Ile Arg Val Leu Glu Arg Phe Asp
            20                  25                  30

Gln Arg Thr Asn Arg Leu Glu Asn Leu Gln Asn Tyr Arg Ile Val Glu
        35                  40                  45

Phe Gln Ser Lys Pro Asn Thr Leu Ile Leu Pro Lys His Ser Asp Ala
    50                  55                  60

Asp Tyr Val Leu Val Leu Asn Gly Arg Ala Thr Ile Thr Ile Val
65                  70                  75                  80

Asn Pro Asp Arg Arg Gln Ala Tyr Asn Leu Glu Tyr Gly Asp Ala Leu
                85                  90                  95

Arg Ile Pro Ala Gly Ser Thr Ser Tyr Ile Leu Asn Pro Asp Asp Asn
            100                 105                 110

Gln Lys Leu Arg Val Val Lys Leu Ala Ile Pro Ile Asn Asn Pro Gly
        115                 120                 125

Tyr Phe Tyr Asp Phe Tyr Pro Ser Ser Thr Lys Asp Gln Gln Ser Tyr
    130                 135                 140

Phe Ser Gly Phe Ser Arg Asn Thr Leu Glu Ala Thr Phe Asn Thr Arg
145                 150                 155                 160

Tyr Glu Glu Ile Gln Arg Ile Ile Leu Gly Asn Glu Asp
                165                 170
```